United States Patent [19]
Ohnishi et al.

[11] Patent Number: 5,463,462
[45] Date of Patent: Oct. 31, 1995

[54] METHOD OF AND APPARATUS FOR INSPECTING HONEYCOMB-SHAPED OBJECT HAVING PLURAL THROUGH HOLES

[75] Inventors: Takao Ohnishi, Niwa; Yukihisa Osugi, Nagoya; Miyuki Muto, Obu, all of Japan

[73] Assignee: NGK Insulators, Ltd., Japan

[21] Appl. No.: 219,381

[22] Filed: Mar. 29, 1994

[30] Foreign Application Priority Data

Mar. 31, 1993 [JP] Japan ................... 5-074516

[51] Int. Cl.⁶ .................................................. G01B 9/02
[52] U.S. Cl. ................................. 356/354; 356/237
[58] Field of Search ............................ 356/237, 345, 356/353, 354

[56] References Cited

U.S. PATENT DOCUMENTS

| | | | |
|---|---|---|---|
| 4,319,840 | 3/1982 | Kondo et al. | 356/241 |
| 4,465,371 | 8/1984 | Pernick | 356/237 |
| 4,513,441 | 4/1985 | Henshaw | 356/237 |
| 4,778,745 | 10/1988 | Leung | 356/237 |
| 5,159,474 | 10/1992 | Franke et al. | 250/208.6 |

FOREIGN PATENT DOCUMENTS

| | | | |
|---|---|---|---|
| 0294643 | 12/1988 | European Pat. Off. | G01N 21/88 |
| 0400777 | 12/1990 | European Pat. Off. | G01N 21/88 |
| 58-155343 | 9/1983 | Japan | G01N 21/88 |

OTHER PUBLICATIONS

Patent Abstracts of Japan, vol. 7, No. 278 (P-242) (1423) Dec. 10, 1983 & JP-A-58 155 343 (Katsuya Yamada) Sep. 16, 1983.

*Primary Examiner*—Samuel A. Turner
*Attorney, Agent, or Firm*—Parkhurst, Wendel & Rossi

[57] ABSTRACT

A parallel light beam is introduced from a collimator lens into through holes defined in a honeycomb-shaped object, and any light emitted from the honeycomb-shaped object is read by a CCD camera through a Fourier-transform lens to produce a Fourier-transform image of the honeycomb-shaped object. The honeycomb-shaped object is tilted such that the axis of the through holes is inclined at a certain angle to the optical axis of the parallel laser beam. If the partitions contain interstices spaced at intervals and light introduced into the through holes passes through such interstices, the Fourier-transform image includes a stripe pattern induced by diffracted light from the interstices. Since the stripe pattern can easily be distinguished from a dot-matrix pattern representing light emitted from the through holes, the interstices contained in the partitions can reliably be detected.

13 Claims, 7 Drawing Sheets

METHOD OF AND APPARATUS FOR INSPECTING HONEYCOMB-SHAPED OBJECT HAVING PLURAL THROUGH HOLES

BACKGROUND OF THE INVENTION

1. Field of the Invention

The present invention relates to a method of and an apparatus for inspecting a honeycomb-shaped object having a plurality of small through holes defined therein, and more particularly to a method of and an apparatus for inspecting a honeycomb-shaped object made of ceramics to determine whether there are interstices developed therein or not.

2. Description of the Prior Art

Honeycomb-shaped objects made of ceramics having a plurality of small through holes defined therein tend to have interstices such as internal cracks or voids developed in thin partitions defining the through holes when the honeycomb-shaped objects are manufactured. The interstices develop due to a difference of contraction between the peripheral portion and the inner portion of the honeycomb-shaped object, as the object starts contracting from the periphery thereof when the object is subjected to a drying process or a sintering process after the object has been formed. If an inspected honeycomb-shaped object is found to have a number of interstices in excess of a predetermined limit, it is discarded as being susceptible to functional or durability problems.

However, since the diameter of the through holes is very small and the partitions that define the through holes are thin, it is highly difficult to confirm the presence of any interstices in inner partitions through a visual inspection process, though it is relatively easy to visually confirm defective interstices in the vicinity of both ends of the honeycomb-shaped object.

According to a Japanese laid-open patent publication No. 58-155343 and a U.S. Pat. No. 4,319,840, there has been proposed a process of inspecting a honeycomb-shaped object for any interstices therein by applying a parallel light beam to the honeycomb-shaped object, inclining the axis of the through holes in the honey- comb-shaped object to the optical axis of the parallel light beam through a certain angle to introduce the parallel light beam into the through holes, and detecting any light beam that has passed out of the through holes to determine whether there are interstices in the honeycomb-shaped object. More specifically, when the honeycomb-shaped object is tilted through the angle, the light beam passing straight through the through holes is interrupted, and any light beam passing through interstices is projected onto a screen. Therefore, it can be determined whether there are interstices in the honeycomb-shaped object by confirming any light beam projected onto the screen.

However, a certain pattern is formed on the screen by dispersed light that is reflected by inner wall surfaces of the through holes, other than the light beam passing straight through the through holes. Such a pattern cannot easily be distinguished from the pattern which is formed on the screen by any light beam that has passed through interstices in the honeycomb-shaped object. Furthermore, where the through holes are slightly curved, the light beam passing straight through the through holes may be applied to the screen depending on the angle between the axis of the through holes and the optical axis of the light beam, and may not be distinguished from any light beam that has passed through interstices in the honeycomb-shaped object. As a result, it may not be possible to determine whether honeycomb-shaped object contains any undesirable interstices.

SUMMARY OF THE INVENTION

It is therefore an object of the present invention to provide a method of and an apparatus for inspecting a honeycomb-shaped object having a plurality of small through holes defined therein to determine or inspect, with greater reliability, whether the honeycomb-shaped object contains any undesirable interstices or not, by applying a parallel light beam into the through holes.

Another object of the present invention is to provide a method of and an apparatus for inspecting a honeycomb-shaped object, within a remarkably shortened period of inspection time, to determine or inspect whether the honeycomb-shaped object contains any undesirable interstices or not, by applying a parallel light beam into the through holes defined in the honeycomb-shaped object.

Still another object of the present invention is to provide a method and an apparatus for inspecting a honeycomb-shaped object automatically and with an enhanced efficiency, to determine or inspect electrically whether the honeycomb-shaped object contains any undesirable interstices or not, by applying a parallel light beam into the through holes defined in the honeycomb-shaped object.

According to the present invention, there is provided a method of inspecting a honeycomb-shaped object having a plurality of through holes defined therein by partitions, comprising the steps of introducing a parallel light beam into the through holes at a given angle with respect to the axis of the through holes, detecting a Fourier-transform image of the honeycomb-shaped object based on light emitted therefrom, and determining whether there are interstices in the partitions based on the detected Fourier-transform image.

Preferably, the step of determining may comprise the steps of measuring the intensity of light in a predetermined zone between periodic patterns of a Fourier-transform image of the through holes on a plane, on which the Fourier-transform image of the honeycomb-shaped object is formed, to make a first decision on whether there are interstices in the partitions based on the measured intensity of light, and if it is determined that there likely are interstices in the partitions based on the measured intensity of light by the first decision, subsequently detecting the difference between the patterns of the Fourier-transform image of the through holes and a Fourier-transform image of any interstices in the partitions to make a second decision on whether there are interstices in the partitions.

According to the present invention, there is also provided an apparatus for inspecting a honeycomb-shaped object having a plurality of through holes defined therein by partitions, comprising first means for introducing a parallel light beam into the through holes at a given angle with respect to the axis of the through holes, second means for detecting a Fourier-transform image of the honeycomb-shaped object based on light emitted therefrom, and third means for determining whether there are interstices in the partitions based on the detected Fourier-transform image.

Preferably, the third means may comprise first decision means for measuring the intensity of light in a predetermined zone between periodic patterns of a Fourier-transform image of the through holes on a plane, on which the Fourier-transform image of the honeycomb-shaped object is formed, to determine whether there are interstices in the partitions based on the measured intensity of light, and second decision means for, if it is not determined that there likely are interstices in the partitions based on the measured intensity of light, subsequently detecting the difference between the patterns of the Fourier-transform image of the through holes and a Fourier-transform image of any interstices in the partitions to determine whether there are interstices in the partitions.

Since the through holes defined in the honeycomb-shaped object are arranged in the shape of a two-dimensional grid, the Fourier-transform image of the honeycomb-shaped object as emitted from the through holes is represented by a dot-matrix pattern. On the other hand, inasmuch as interstices formed in the partitions are spaced at a certain interval, i.e., in the shape of a one-dimensional diffraction grating, the Fourier-transform image of any interstices is represented by a stripe pattern. Since the Fourier-transform image of any interstices and the Fourier-transform image of the through holes are clearly different in pattern from each other, the S/N ratio for detecting any interstices based on the differently shaped patterns is so high that the interstices formed in the partitions can easily and reliably be identified.

For detecting whether there are interstices in the partitions based on the Fourier-transform images, as described above, the intensity of light is measured in a predetermined zone between periodic patterns of a Fourier-transform image of the through holes on a plane on which the Fourier-transform image of the honeycomb-shaped object is formed to make a first decision on whether there are interstices in the partitions based on the measured intensity of light, and if it is not determined that there are no interstices in the partitions, the difference between the Fourier-transform image of the through holes and a Fourier-transform image of any interstices in the partitions are subsequently determined to make a second decision on whether there are interstices in the partitions. Since the intensity of light can be detected from an image signal outputted by the second means, it is possible to quickly determine whether there are interstices in the partitions based on the measured intensity of light. Inasmuch as most honeycomb-shaped objects have no interstices, it is usually enough to determine whether there are interstices in the partitions based on the measured intensity of light, and any subsequent processing steps may be dispensed with, resulting in a reduction in the time required for inspecting the honeycomb-shaped object. If it is not determined that there are no interstices in the partitions based on the measured intensity of light, then it is determined whether there are interstices in the partitions based on the difference between the patterns of the Fourier-transform image of the through holes and a Fourier-transform image of interstices. Accordingly, any interstices in the partitions can reliably be detected.

The above and other objects, features, and advantages of the present invention will become apparent from the following description when taken in conjunction with the accompanying drawings which illustrate a preferred embodiment of the present invention by way of example.

DETAILED DESCRIPTION OF THE PREFERRED EMBODIMENT

Figure 1:
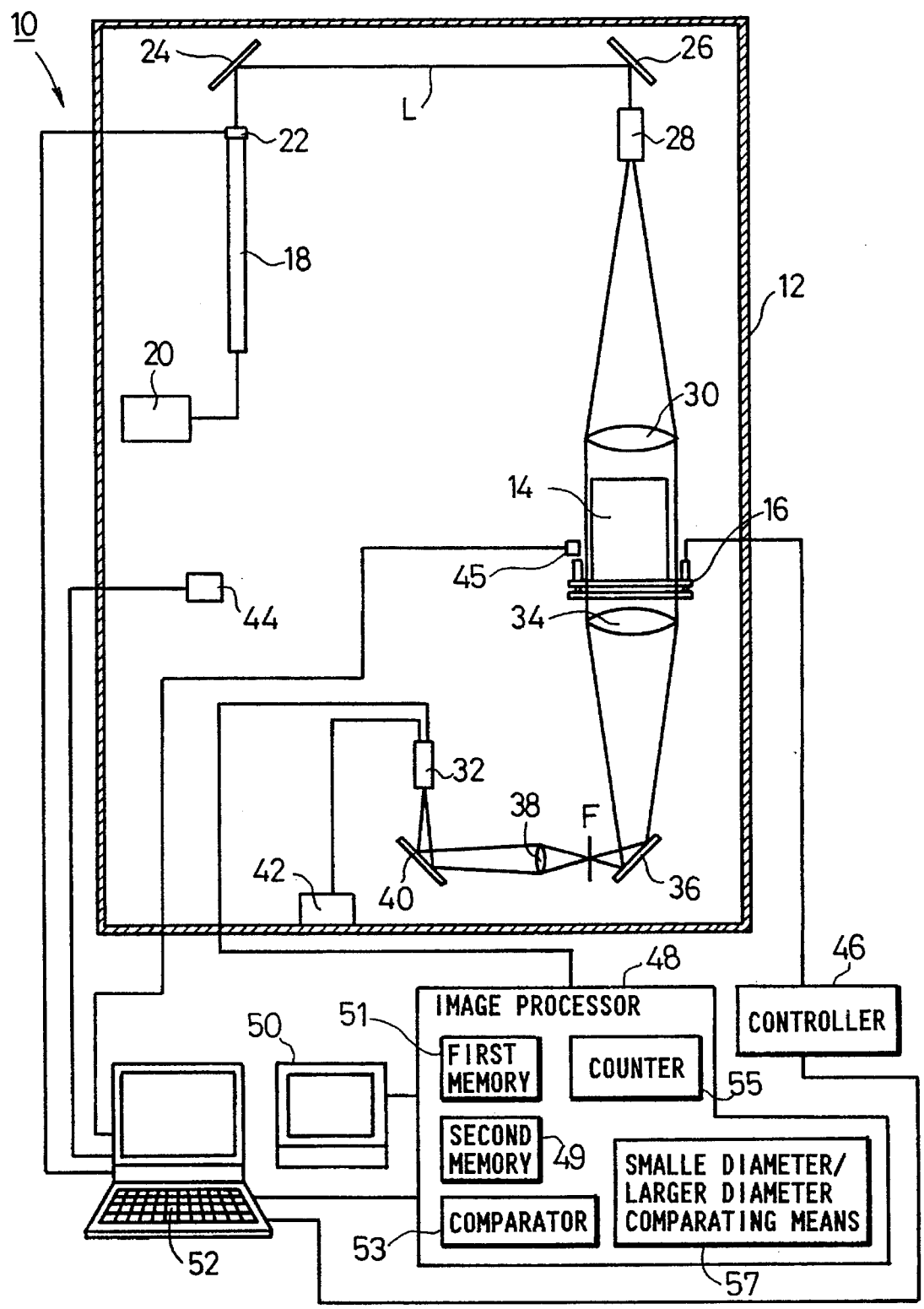
FIG. 1 is a schematic view, partly in block form, of an apparatus for inspecting a honeycomb-shaped object having a plurality of small through holes defined therein according to the present invention.

As shown in FIG. 1, an apparatus, generally designated by the reference numeral 10, for inspecting a honeycomb-shaped object having a plurality of small through holes defined therein according to the present invention has a light-shielding housing 12 which houses therein a tilting mechanism 16 for supporting a honeycomb-shaped object 14 fed by a feed mechanism (not shown) and angularly moving or tilting the honeycomb-shaped object 14 about two axes. The apparatus 10 also comprises an He—Ne laser 18 for emitting a laser beam L to be applied to the honeycomb-shaped object 14, a power supply 20 for energizing the He—Ne laser 18, an electronic shutter 22 mounted on the tip end of the He—Ne laser 18, a pair of reflecting mirrors 24, 26 for fully reflecting the laser beam L emitted from the He—Ne laser 18, a spatial filter 28 for spreading the laser beam L and removing disturbance from the laser beam L, a collimator lens 30 for converting the laser beam L into a parallel laser beam L and applying the parallel laser beam L to the honeycomb-shaped object 14, a Fourier-transform lens 34 for generating a Braunhofer-diffraction image produced at an infinite point by the diffraction of the beam emitted from the honeycomb-shaped object 14, on a finite focal plane F, a reflecting mirror 36, a focusing lens 88, a reflecting mirror 40, a CCD camera 32 for inputting an image, and a power supply 42 for energizing the CCD camera 32. The tilting mechanism 16 is provided with a photo-electric sensor or a proximity switch 45 for detecting whether there is the honeycomb-shaped object 14 put thereon or not. The housing 12 also houses a proximity switch 44 for detecting whether the lid of the housing 12 is opened or closed, thereby to prevent an accident from occurring during an inspection process.

The apparatus 10 also includes a controller 46 for controlling the tilting mechanism 16, an image processor 48 for processing an image signal read from the CCD camera 32, a monitor display unit 50 for displaying an image processed by the image processor 48, and a personal computer 52 connected to the controller 46, the image processor 48, the electronic shutter 22, and the proximity switch 44.

Figure 2:
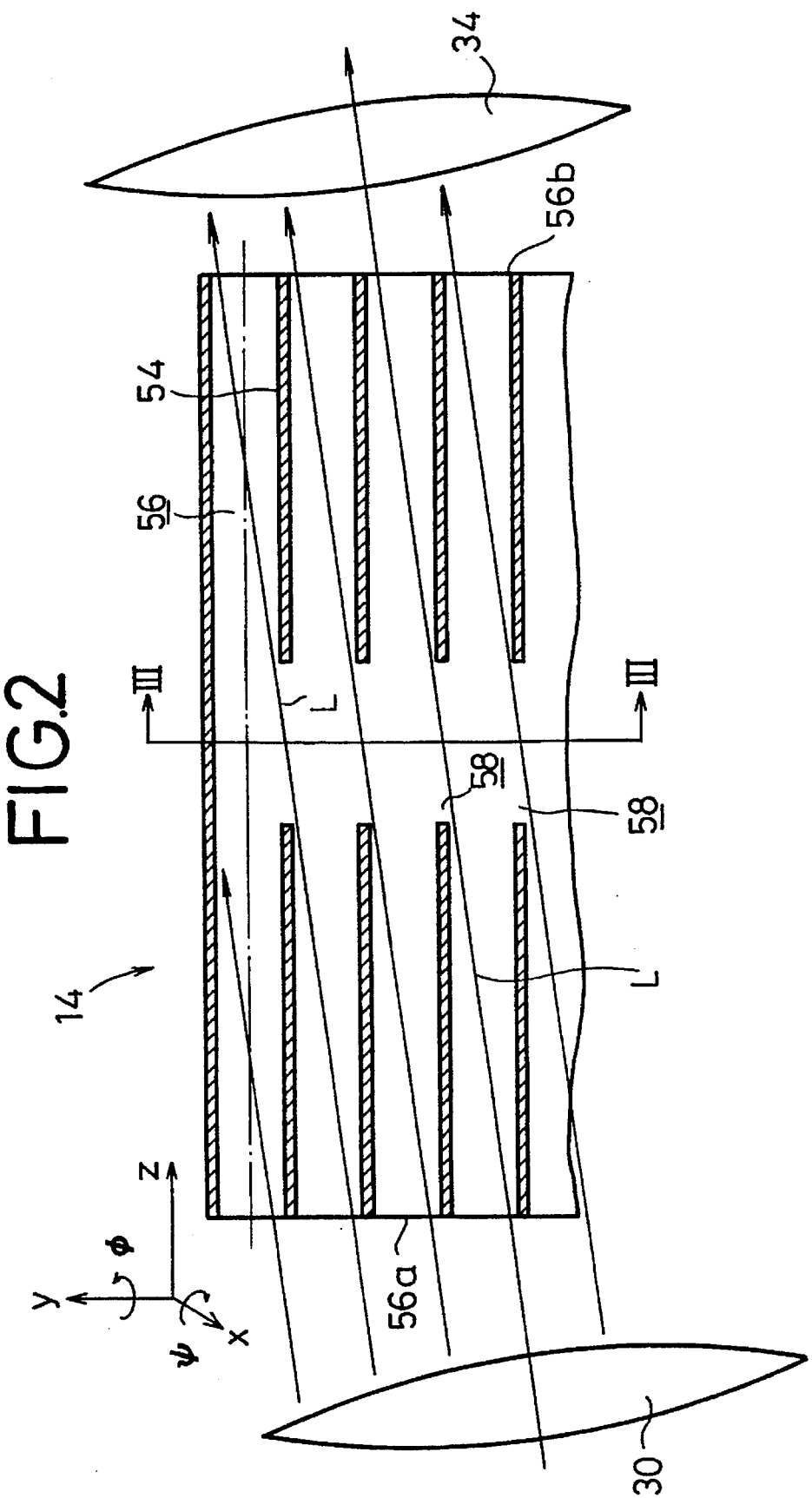
FIG. 2 is an enlarged fragmentary cross-sectional view of a portion of the apparatus shown in FIG. 1.
Figure 3:
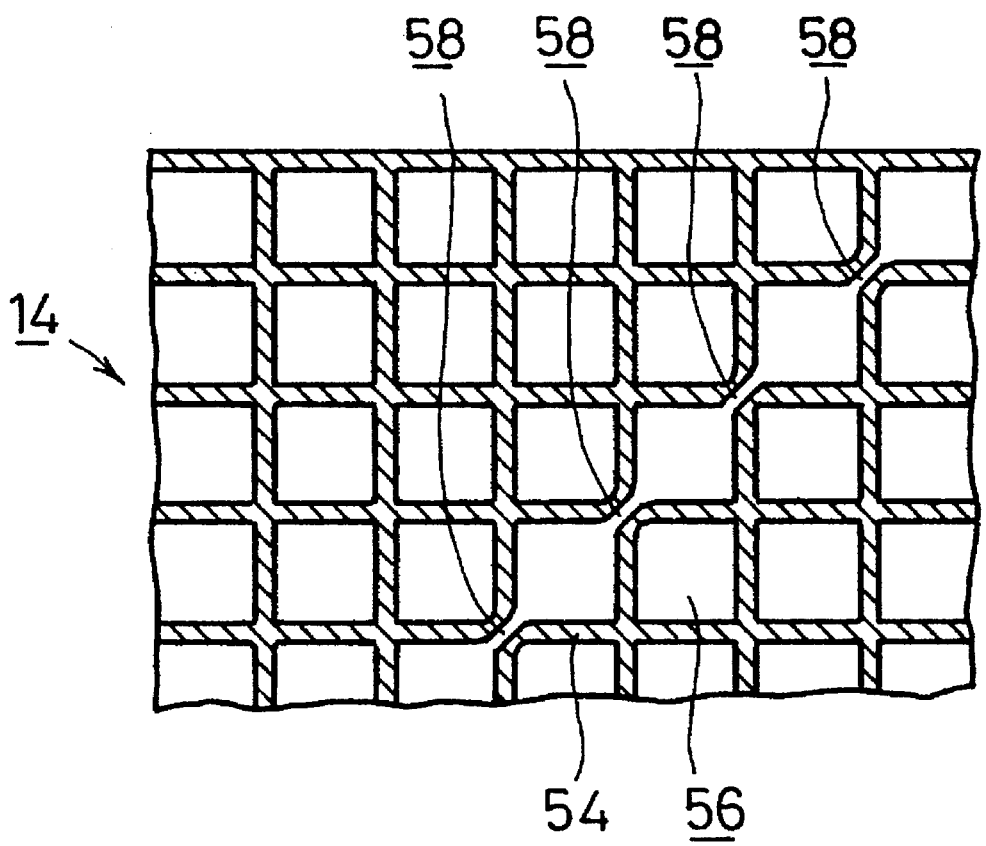
FIG. 3 is an enlarged cross-sectional view of a honeycomb-shaped object.

As shown in FIGS. 2 and 3, the honeycomb-shaped object 14 has a plurality of parallel through holes 56 defined and divided by a plurality of parallel partitions 54. The cross-sectional shape of the through hole 56 is not limited to one shown in FIGS. 2 and 3, but it may be a triangle, a rectangle, a hexagon and so forth.

The apparatus 10 can detect defects such as cracks or crevices, hereinafter referred to as interstices 58, in the partitions 54 of the honeycomb-shaped object 14 based on the detection principle described below.

Figure 7:
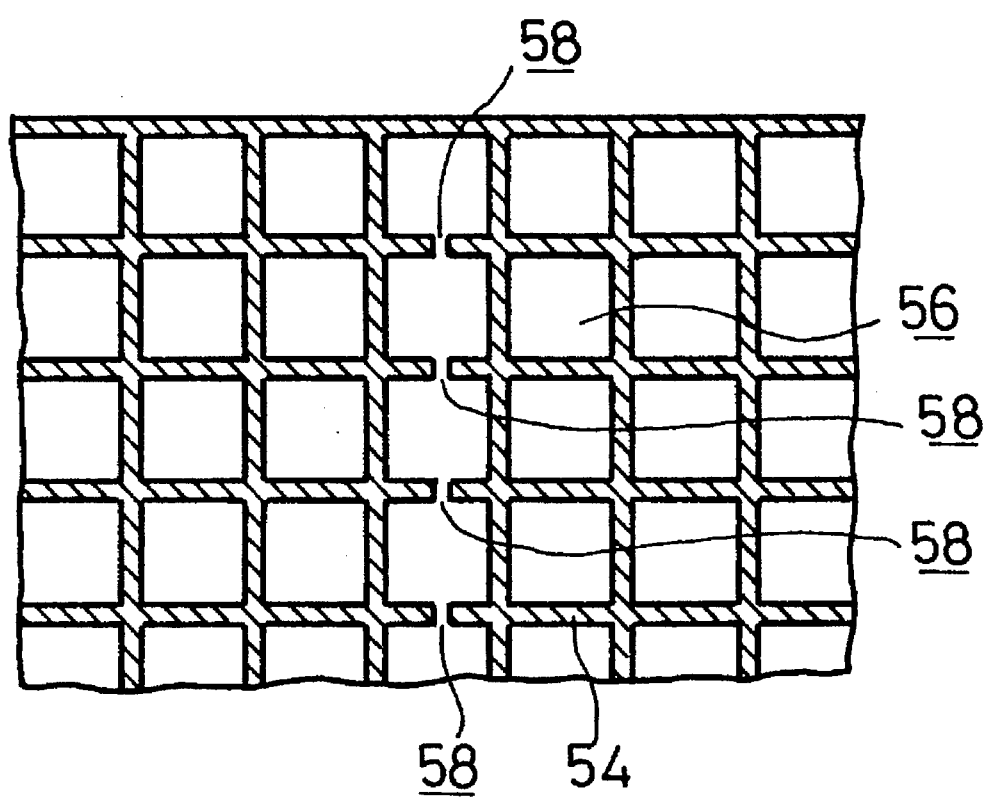
FIG. 7 is an enlarged cross-sectional view of another honeycomb-shaped object.

As shown in FIG. 2, a parallel laser beam L, which is inclined at a certain angle to the axis of the through holes 56, indicated by the dot-and-dash line, in the honeycomb-shaped object 14, is introduced into the through holes 56 from ends 56a thereof. Here, the honeycomb-shaped object 14 has the partitions 54 of 0.05 to 2.0 mm thick and the through holes 56 at a density of 5 to 1,500 per square inch. If the partitions 54 have interstices 58, then the parallel laser beam L passes through the interstices 58, and are emitted out of the through holes 56 from their opposite ends 56b. The parallel laser beam L then travels through the Fourier-transform lens 34. As shown in FIG. 3, the interstices 58 are positioned at certain intervals on one diagonal line (see also FIG. 2), and hence virtually form a diffraction grating. Therefore, the parallel laser beam L that has passed through the interstices 58 and has been emitted out of the honeycomb-shaped object 14 is focused by the Fourier-transform lens 34 as a Fourier-transform image of interstices 58 on the focal plane F, as described later (see FIG. 5). Since the interstices 58 are arrayed at certain intervals on one diagonal line, the Fourier-transform image thereof represents a pattern of parallel oblique stripes spaced at constant intervals. On the other hand, a Fourier-transform image of through holes 56 represents a dot-matrix pattern because the through holes 56 are arranged in a two-dimensional grid. Since the Fourier-transform image of interstices 58 is widely different from the Fourier-transform image of through holes 56, any interstices 58 can easily and reliably be detected based on the difference between those Fourier-transform images. Incidentally, there are cases where the interstices 58 are arranged on one vertical or horizontal straight line as shown in FIG. 7, other than one diagonal line.

Figure 4:
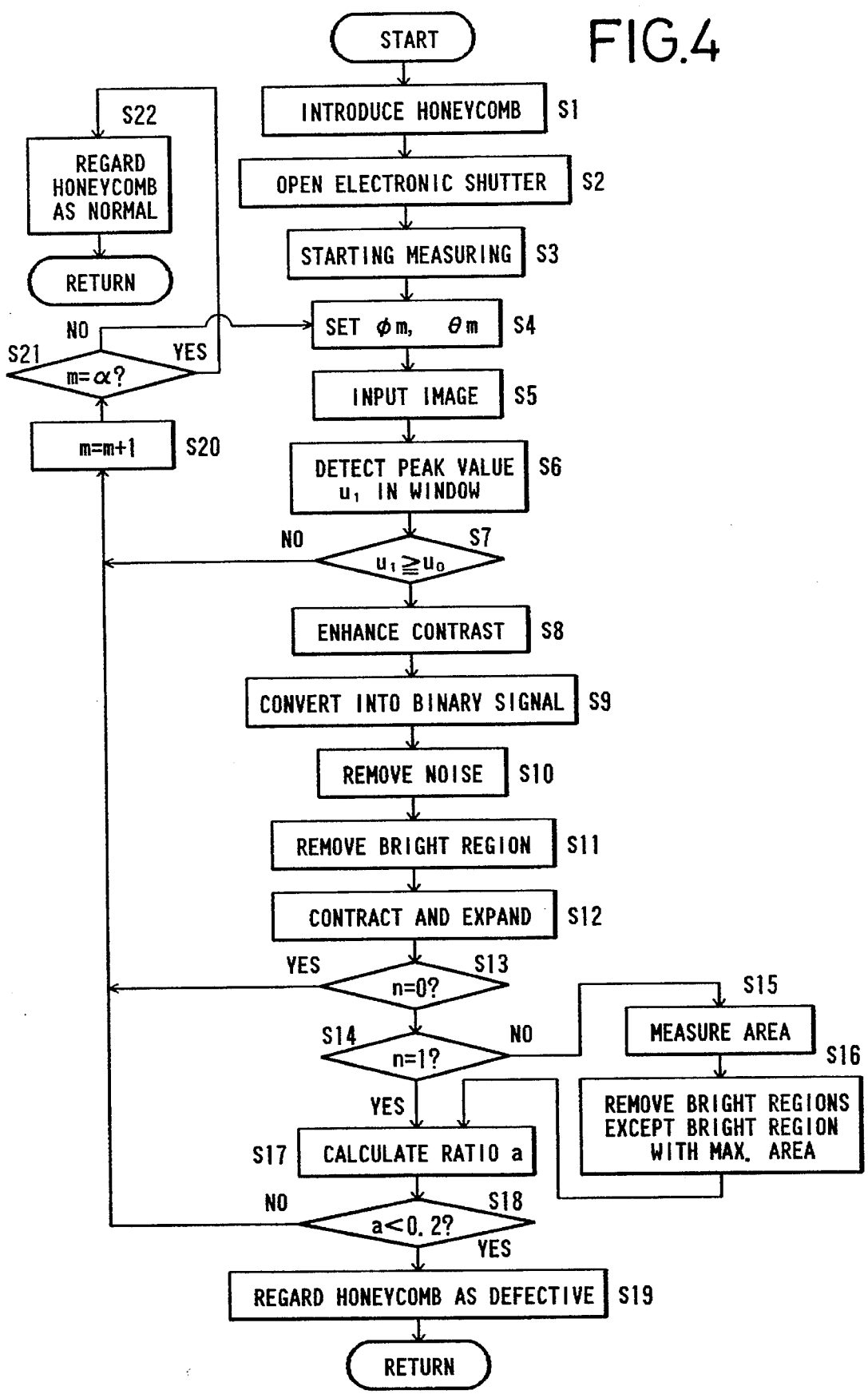
FIG. 4 is a flowchart of a processing sequence of a method of inspecting a honeycomb-shaped object having a plurality of small through holes defined therein according to the present invention.

Now, an inspection process will be described in detail below with reference to the processing sequence shown in FIG. 4, which is executed by the personal computer 52. First, as shown in FIG. 4, the honeycomb-shaped object 14 is delivered onto the tilting mechanism 16 in the apparatus housing 12 by the non-illustrated feed mechanism in a step S1. When the honeycomb-shaped object 14 is placed on the tilting mechanism 16, a detection signal is outputted from the photo-electric sensor 45, and the detection signal is fed to the personal computer 52 through the controller 46. In response to this signal indicating that the honeycomb-shaped object 14 has been placed on the tilting mechanism 16, the personal computer 52 supplies an opening signal to the electronic shutter 22 to open the electronic shutter 22 in a step S2. Then, the personal computer 52 starts a measuring operation in a step S3. The personal computer 52 then applies a signal to enable the controller 46 to actuate the tilting mechanism 16 for tilting the through holes 56 in the honeycomb-shaped object 14 from the optical axis through angles $\phi_m$, $\theta_m$ about respective axes in a step S4. If the inspection process is effected for the first time, then the suffix (the number of decision cycles) m=1 for the angles $\phi_m$, $\theta_m$.

The He—He laser 18 emits a laser beam L toward the reflecting mirror 24, which reflects the laser beam L toward the reflecting mirror 26. The laser beam L is then reflected by the reflecting mirror 26 and travels through the spatial filter 28 and the collimator lens 30, which converts the laser beam L into a parallel laser beam L that passes through the honeycomb-shaped object 14. As shown in FIG. 2, the parallel laser beam L from the collimator lens 30 enters the through holes 56, which has been tilted through the angles $\phi_m$, $\theta_m$ from the ends 56a thereof. The laser beam L is then emitted out of the through holes 56 from the ends 56b, and focused by the Fourier-transform lens 34 as a Fourier-transform image on the focal plane F via the reflecting mirror 36. The Fourier-transform image formed on the focal plane F is read by the CCD camera 32 through the focusing lens 38 and the reflecting mirror 40, and an image signal is supplied from the CCD camera 32 to the image processor 48 in a step S5. The image signal is then supplied from the image processor 48 to the monitor display unit 50, which displays the Fourier-transform image.

The Fourier-transform image shown in FIG. 3, which is obtained from the honeycomb-shaped object 14 including interstices 58 therein, and displayed on the monitor display unit 50, will be described below with reference to FIG. 5.

If the honeycomb-shaped object 14 is normal with the through holes 56 having a straight axis and the partitions 54 having no interstices 58, then no image is displayed on the display screen of the monitor display unit 50. No image is displayed on the display screen of the monitor display unit 50 because the parallel laser beam L that has entered the through holes 56 cannot travel straight, but is dispersed in the through holes 56, because the through holes are tilted by a certain angle by the tilting mechanism 16.

If the honeycomb-shaped object 14 is of such a nature that the through holes 56 have a straight axis and the partitions 54 have interstices 58, then the parallel laser beam L may pass through the inclined through holes 56 and be emitted out of the honeycomb-shaped object 14. In this case, the interstices 58 are periodically arranged on one straight line which serve as a diffraction grating, and the display screen of the monitor display unit 50 displays a pattern of bright stripes 60a which represent a Fourier-transform image of the interstices 58 arranged on the straight line (see FIG. 5).

On the contrary, if the honeycomb-shaped object 14 is of such a nature that the through holes 56 have a curved axis but the partitions 54 have no interstices, then the parallel laser beam L may occasionally pass through the through hole 56 inclined at a certain angle and emitted from the honeycomb-shaped object 14. In such an occasion, the display screen of the monitor display unit 50 displays a matrix of bright dots or spots 60b which represent a Fourier-transform image of the through holes 56 arranged on a two-dimensional grid. In this occasion, since the through holes 56 are curved, the laser beam L emitted out of the through holes 56 is dispersed in the through holes 56. The dispersed light is diffracted, producing bright areas 60c around the bright spots 60b on the display screen of the monitor display unit 60.

If the honeycomb-shaped object 14 is of such a nature that the through holes 56 have a curved axis and the partitions 54 have interstices 58, then the parallel laser beam L that has passed through the interstices 58 and been emitted out of the honeycomb-shaped object 14, which are inclined through the angles $\phi_m$, $\theta_m$, produces, on the display screen of the monitor display unit 50, a Fourier-transform image of the through holes 56 that is composed of bright spots 60b and bright areas 60c, and a Fourier-transform image of interstices 58 that is composed of bright stripes 60a.

Figure 8:
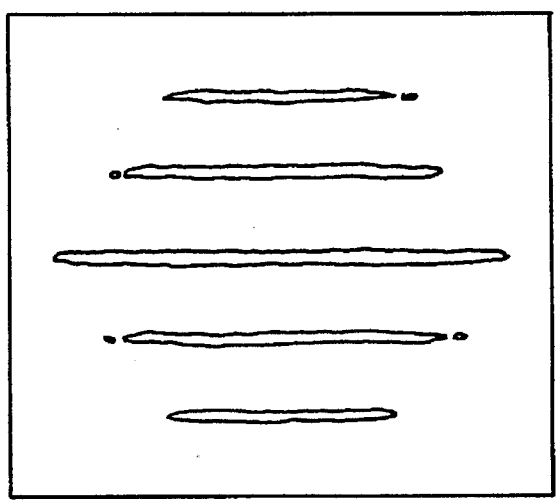
FIG. 8 is a diagram illustrative of the manner in which an image signal is processed to inspect the honeycomb-shaped object shown in FIG. 7.
Figure 9:
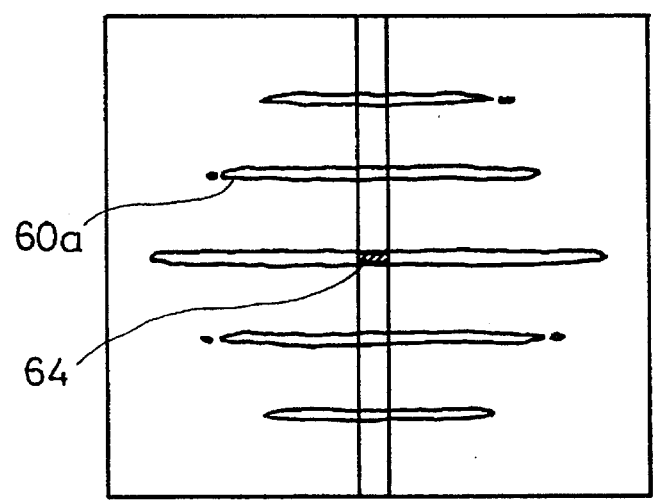
FIG. 9 is a diagram illustrative of the manner in which an image signal is processed to inspect the honeycomb-shaped object shown in FIG. 7.

If the ends 56a, 56b of the honeycomb-shaped object 14 are inclined beforehand, then the axis of the through holes 56 may be brought into alignment with the optical axis of the parallel laser beam L when the honeycomb-shaped object 14 is tilted. The parallel laser beam L may now pass through the through holes 56, forming a matrix of bright spots on the display screen of the monitor display unit 50. For the interstices 58 shown in FIG. 7, a Fourier-transform image is displayed as shown in FIG. 8.

Where some bright image is displayed on the display screen of the monitor display unit 50, the image processor 48 effects the following operation on the image signal: First, the image processor 48 establishes a window 62 with respect to the image signal representing the bright image as shown in FIG. 5. The window 62 is positioned vertically (extending horizontally) intermediate between two adjacent arrays of bright spots 60b and bright areas 60c, as shown in FIG. 5. The window 62 may be positioned horizontally (extending vertically) as shown in FIG. 9. Then, the image processor 48 detects the brightness $u_1$ of each block 64 composed of a vertical array of several pixels within the window 62, and then detects the peak value of the brightness $u_1$ in the window 62 in a step S6. Thereafter, the image processor 48 stores the detected peak value in a second memory 49 in the image processor 48 and compares the detected peak value with a reference brightness $u_0$ preset and stored in a first memory 51 beforehand, by a comparator 53 in a step S7. Here, it is possible to send the detected peak brightness $u_1$ directly to the personal computer 52 and compare it with the reference brightness $u_0$ preset in the computer program. If the peak brightness $u_1$ is lower than the reference brightness $u_0$, then the image processor 48 determines that no interstices are detected. This is because if there are interstices 58 in the partitions 54 of the honeycomb-shaped object 14, then a pattern of bright stripes 60a representative of a Fourier-transform image of such interstices 58 always appears in the window 62. Therefore, if the peak brightness $u_1$ is lower than the reference brightness $u_0$, then control returns to the step S4, and the personal computer 52 controls the controller 46 to actuate the tilting mechanism 16 to tilt the honeycomb-shaped object 14 through new angles $\phi_{m+1}$, $\theta_{m+1}$. Thereafter, the steps S5 through S7 are repeated.

The image processing of the steps S5 through S7 was effected by image processing apparatuses SPICCA-II made by Nippon Avionics Co. and PIP-4000 made by ADS Co. Reference was made to such as "Image Analysis Handbook" (Tokyo Univ. Press) and "Computer Vision" (Marubun Publishing).

Figure 5:
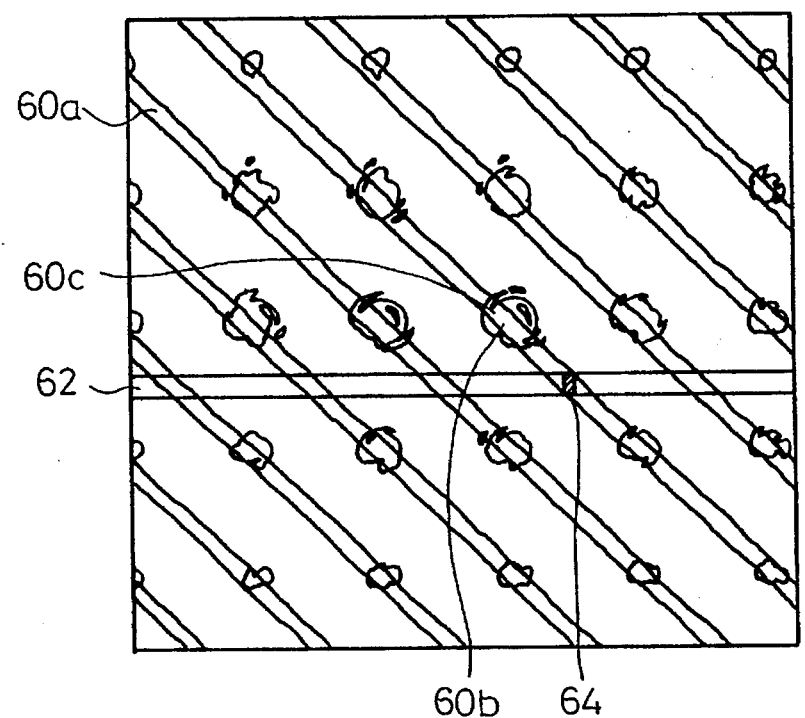
FIG. 5 is a diagram illustrative of the manner in which an image signal is processed to inspect the honeycomb-shaped object.

In the steps S6, S7, as shown in FIG. 5, the image processor 48 only detects the brightness $u_1$ from the image signal which is outputted from the CCD camera 32 as representing the window 62, and compares the peak value of the brightness $u_1$ with the reference brightness $u_0$. Since the image processor 48 does not process the image signal itself, its operation is very quick.

Inasmuch as the window 62 is positioned vertically intermediate between two adjacent arrays of bright spots 60b and bright areas 60c, these bright spots 60b and bright areas 60c are excluded when the brightness is detected within the window 62 in the step S6. Consequently, the execution of a step S8 and following steps which would be carried out even in the absence of interstices 58 in the partitions 54 is made less frequent, resulting in a reduction in the speed of the inspection process.

If there are interstices 58 developed in the partitions 54 of the honeycomb-shaped object 14, a Fourier-transform image composed of bright stripes 60a which is produced by diffracted light from the interstices 58 is displayed on the display screen of the monitor display unit 50. As shown in FIG. 5, when the window 62 is established vertically intermediate between two adjacent arrays of bright spots 60b and bright areas 60c, the bright stripes 60a are contained in the window 62. Thus, the brightness $u_1$ of a block 62 which includes a bright stripe 60a is higher than the reference brightness $u_0$, with the result that the interstices 58 can reliably be detected.

If the honeycomb-shaped object 14 is normal with no interstices 58 present therein, the peak value of the brightness $u_1$ is lower than the reference brightness $u_0$ ($u_1 < u_0$), and the steps S4–S7 are repeated. Even if the honeycomb-shaped object 14 is normal, however, diffracted light or other dispersed light may enter the window 62, and the peak value of the brightness $u_1$ may become equal or higher than the reference brightness $u_0$ ($u_1 \geq u_0$). In this case, it is impossible to determine whether there are interstices 58 in the partitions 54 or not, solely based on the comparison of brightness levels. To determine whether there are interstices 58 in the partitions 54 or not, the pattern of a displayed Fourier-transform image is identified in the following manner:

The contrast of the displayed Fourier-transform image is enhanced in a step S8, and the Fourier-transform image is converted into a binary signal in a step S9. Then, small noise due to a speckle pattern generated by light dispersed by the partitions 54 in the through holes 56 is removed in a step S10. In the noise reduction of the step S10, a conventional image processing method is used. Noise components represented by an area smaller than a reference pattern area, are removed. If the image contains a bright region larger than a predetermined area, then such a bright region is removed in step S11. This is a reverse process of the step S10, in which a region larger than a predetermined area is removed. The reason for removing such a bright region is as follows: The through holes 56 may be slightly curved and the parallel laser beam L may pass through the curved through holes 56 even though the axis of the through holes 56 is inclined to the optical axis of the parallel laser beam L through the angles $\phi_m$, $\theta_m$. When this happens, halation may be brought about. When halation is produced, a bright region induced by the halation is relatively large, and hence should be removed in a step similar to the step S11. After the step S11, the image is subjected to dilation and erosion to remove small round spots in a step S12. Since the Fourier-transform image of through holes 56 is composed of small round spots, most of them are removed in the step S12. However, the Fourier-transform image of interstices 58 is not removed as it is composed of stripes.

Then, the image processor 48 counts bright regions displayed on the display screen of the monitor display unit 50. If the count n is 0 in a step S13, then since any diffracted light which would otherwise be caused by interstices 58 is not detected, and control returns from the step S13 to the step S4 in which the honeycomb-shaped object 14 is tilted through new angles $\phi_{m+1}$, $\theta_{m+1}$. If the count n is 1 or greater in the step S13, then there is a possibility that there are interstices 58 in the partitions 54, and control proceeds to a step S14.

Figure 6:
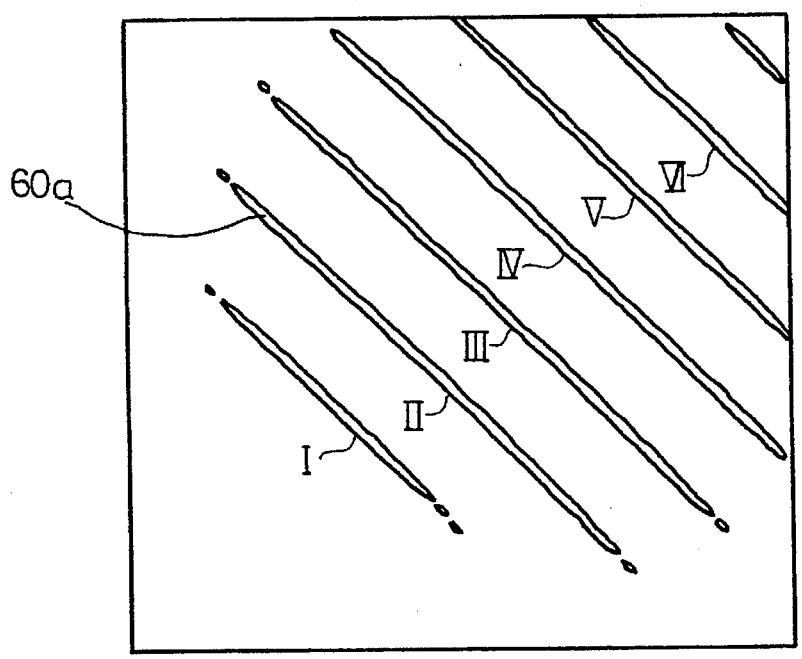
FIG. 6 is a diagram illustrative of the manner in which an image signal is processed to inspect the honeycomb-shaped object.

The step S14 determines whether the count n is 1 or not. If there are a plurality of bright regions displayed on the display screen, then the image processor 48 calculates the areas of the bright regions in a step S15, and then removes all the other bright regions than the bright region which has the maximum area, i.e., making the number of displayed bright regions equal to 1, in a step S16. This is because it would be time-consuming to decide on all bright regions subsequently. Then, in a step S17, the image processor 48 calculates the ratio of the smaller diameter to larger diameter (=a) of the bright region which has the maximum area produced in the step S16 or the single bright region found in the step S14. For example, in a case where regions denoted by I, II, III, IV, V and VI have area values 5, 7, 8, 10 and 6, respectively in FIG. 6, it is time saving to give a command to the personal computer 52 to remove regions having area values less than 9, and remove regions other than IV, without determining respective area values. When the number of the largest bright region remaining after the removal, or the number of bright regions is 1 in the step S14, a ratio of a=smaller diameter/larger diameter of the bright region is calculated. The image processor 48 thereafter determines whether the ratio a is smaller than an empirical value 0.3 or not by a smaller diameter/larger diameter comparating means 57 in the image processor 48 in steps S17 and S18. This decision step serves to determine whether the bright region is of a long slender shape or not. If the bright region is of a long slender shape, then it is judged as being produced by diffracted light that has passed through an interstice 58 in a partition 54. If the ratio a is smaller than 0.3 in the step S19, then the honeycomb-shaped object 14 is regarded as containing interstices 58, as shown in FIG. 6, and hence being defective in a step S19. The honeycomb-shaped object 14 is now discharged from the apparatus 10 in a step S 20. If the ratio a is equal to or greater than 0.3 in the step S18, then the bright area is judged as being caused by other than any interstices, and control returns from the step S18 to the step S4. Judging method by using the ratio of smaller diameter to larger diameter is known from the aforementioned references.

If no interstices are found in the partitions 54 in the steps S7, S13, S18, then the number m of decision cycles is incremented in a step S20, and thereafter it is determined whether the number m of decision cycles has reached a predetermined number a, 4–8 for instance, or not in a step S21. If the number m of decision cycles has reached the predetermined number a, then the honeycomb-shaped object 14 is judged as being normal in a step S22, and the inspection process is ended. The honeycomb-shaped object 14 is discharged from the apparatus 10.

According to the above inspection process and the apparatus 10 which carries out the inspection process, as described above, both a stripe pattern composed of bright stripes 60a which represents a Fourier-transform image of interstices 58 and a dot-matrix pattern composed of bright spots 60b and bright areas 60c which represents a Fourier-transform image of through holes 56 are detected. Since the bright spots 60b and bright areas 60c which make up a dot-matrix pattern and are produced by diffracted light having passed through the through holes 56 in the shape of a two-dimensional grid, and the bright stripes 60a which make up a stripe pattern and are produced by diffracted light having passed through the interstices 58 are clearly different in shape from each other, the S/N ratio for detecting the interstices 58 based on the differently shaped patterns is so high that the interstices 58 formed in the partitions 54 can easily and reliably be identified.

Because the window 62 is positioned vertically intermediate between two adjacent arrays of bright spots 60b and bright areas 60c, these bright spots 60b and bright areas 60c are excluded when the brightness peak is detected within the window 62 in the step S6. Consequently, the execution of the step 8 and following steps is made less frequent which would be caused if a brightness peak produced by light having passed through the through holes 56 were higher than a predetermined value in the step S7, representing a bright stripe 60a, even in the absence of interstices 58 in the partitions 54. Therefore, the speed of the overall inspection process is increased.

While the laser beam is employed as light for irradiating the honeycomb-shaped object 14, other coherent light may be employed, and hence any means for producing such coherent light may replace the He—Ne laser 18.

Although a certain preferred embodiment of the present invention has been shown and described in detail, it should be understood that various changes and modifications may be made therein without departing from the scope of the appended claims.

What is claimed is:

1. A method of inspecting a honeycomb-shaped object having a plurality of through holes defined therein by partitions, comprising the steps of:

introducing a parallel light beam into the through holes at an angle with respect to an axis of the through holes;

generating at least one Fourier-transform image from the honeycomb-shaped object by passing light through the honeycomb-shaped object; and determining whether there are interstices in the partitions based on the at least one Fourier-transform image, by observing whether said at least one Fourier-transform image includes a Fourier-transform image of interstices in the partitions, which includes a pattern of periodic images, said periodic images including equidistantly spaced parallel stripes.

2. A method according to claim 1, wherein said at least one Fourier-transform image includes a Fourier-transform image of the through holes which includes a pattern of periodic images, and said step of determining comprises the steps of:

measuring an intensity of light in a predetermined zone located between periodic images of the Fourier-transform image of the through holes on a plane, to detect presence of interstices in the partitions based on the measured intensity of light; and confirming the presence of interstices in the partitions when said measured intensity of light indicates the presence of interstices, by subsequently detecting the difference between the patterns of periodic images of the Fourier-transform image of the through holes and the Fourier-transform image of interstices in the partitions.

3. A method according to claim 2, wherein the pattern of periodic images of the Fourier-transform of the through holes are bright regions, and the predetermined zone is intermediately between adjacent bright regions which represent the through holes in the honeycomb-shaped object.

4. A method according to claim 3, wherein said intensity of light comprises the brightness of light.

5. A method according to claim 4, wherein said step of measuring includes the steps of:

comparing a peak value of the brightness of light measured in the predetermined zone with a preset reference value; and determining the presence of interstices in the partitions when said peak value is higher than the reference value.

6. A method according to claim 2, wherein said step of confirming includes:

counting bright regions representing the periodic images of at least one of the Fourier-transform images; and calculating a ratio of a small dimension to a large dimension of a selected bright region when the number of bright regions is at least one.

7. A method according to claim 6, wherein interstices in the partitions are present if the ratio of the small dimension to the large dimension is smaller than 0.3.

8. An apparatus for inspecting a honeycomb-shaped object having a plurality of through holes defined therein by partitions, comprising:

first means for introducing a parallel light beam into the through holes at an angle with respect to an axis of the through holes;

second means for generating at least one Fourier-transform image from the honeycomb-shaped object based on light which has passed through the honeycomb-shaped object; and third means for determining whether there are interstices in the partitions based on the at least one Fourier-transform image, by observing whether said at least one Fourier-transform image includes a Fourier-transform image of interstices in the partitions, which includes a pattern of periodic images, said periodic images including equidistantly spaced parallel stripes.

9. An apparatus according to claim 8, wherein said first means comprises an optical system including a laser beam source for emitting a laser beam as said parallel light beam, and a tilting mechanism for tilting the honeycomb-shaped object through said angle.

10. An apparatus according to claim 8, wherein said at least one Fourier-transform image includes a Fourier-transform image of the through holes which includes a pattern of periodic images, and said third means comprises:

first decision means for measuring an intensity of light in a predetermined zone located between periodic images of the Fourier-transform image of the through holes on a plane to detect presence of interstices in the partitions based on the measured intensity of light; and second decision means for confirming the presence of interstices in the partitions when said measured intensity of light indicates the presence of interstices, by subsequently detecting the difference between the patterns of periodic images of the Fourier-transform image of the through holes and the Fourier-transform image of interstices in the partitions.

11. An apparatus according to claim 10, wherein the pattern of periodic images of the Fourier-transform of the through holes are bright regions, and said first decision means comprises image display means for displaying an image, and means for establishing a window between adjacent bright regions which represent the through holes in the honeycomb-shaped object, displayed on said image display means.

12. An apparatus according to claim 11, wherein said first decision means further comprises first memory means for storing a reference brightness signal, second memory means for storing a brightness signal representing one of said bright regions displayed in said window on said image display means, and comparing means for comparing an output signal from said first memory means and an output signal from said second memory means.

13. An apparatus according to claim 10, wherein said second decision means comprises means for counting bright regions representing the periodic images of at least one of the Fourier-transform images, and means for comparing a small dimension to a large dimension of a selected bright region.

* * * * *